United States Patent
Hahn

[11] Patent Number: 5,838,429
[45] Date of Patent: Nov. 17, 1998

[54] APPARATUS FOR MEASURING PHYSIOLOGICAL PARAMETERS OF BLOOD GUIDED IN AN EXTRACORPOREAL CIRCULATORY SYSTEM

[75] Inventor: Andreas Hahn, Sauerlach, Germany

[73] Assignee: Stöckert Instrumente GmbH, Munich, Germany

[21] Appl. No.: 855,918

[22] Filed: May 14, 1997

[30] Foreign Application Priority Data

May 14, 1996 [DE] Germany .................. 196 19 513.6

[51] Int. Cl.⁶ .................. G01N 33/48; G01J 1/04
[52] U.S. Cl. .............. 356/39; 356/446; 356/236; 600/322; 600/326
[58] Field of Search .............. 356/39, 446, 236, 356/41, 40; 600/322, 323, 324, 326; 250/228

[56] References Cited

U.S. PATENT DOCUMENTS

| | | |
|---|---|---|
| 4,320,978 | 3/1982 | Sato .................. 250/228 |
| 4,444,498 | 4/1984 | Heinemann . |
| 4,485,820 | 12/1984 | Flower . |
| 4,523,853 | 6/1985 | Rosenbladt et al. . |
| 4,867,559 | 9/1989 | Bach . |
| 4,883,953 | 11/1989 | Koashi et al. . |
| 4,942,305 | 7/1990 | Sommer . |
| 5,164,597 | 11/1992 | Lodder .................. 250/228 |
| 5,251,004 | 10/1993 | Doiron et al. . |
| 5,422,483 | 6/1995 | Ando et al. . |
| 5,533,509 | 7/1996 | Koashi et al. .............. 356/41 |

FOREIGN PATENT DOCUMENTS

| | | |
|---|---|---|
| 31 38 878 A1 | 4/1983 | Germany . |
| 35 34 973 A1 | 4/1987 | Germany . |
| 40 24 929 A1 | 2/1992 | Germany . |
| WO 85/00426 | 1/1985 | WIPO . |

*Primary Examiner*—Frank G. Font
*Assistant Examiner*—Zandra V. Smith
*Attorney, Agent, or Firm*—Scully, Scott, Murphy & Presser

[57] ABSTRACT

The invention relates to an apparatus for measuring physiological parameters of blood conveyed within an extracorporeal circulatory system. Two light sources (1a, 1b) emit light of varying wavelength into a spherical cavity (3) that comprises a reflective inner surface (3a). Light sensor means (2) receives part of the light propagating within the cavity (3). A tube portion of the extracorporeal circulation can be inserted into a second cavity (4) such that the light (La, Lb) emitted by the light sources encounters the boundary surface between the blood and an inner wall of the tube. The light returns to the cavity (3) at least to an extent by means of reflection and/or transmission.

32 Claims, 2 Drawing Sheets

APPARATUS FOR MEASURING PHYSIOLOGICAL PARAMETERS OF BLOOD GUIDED IN AN EXTRACORPOREAL CIRCULATORY SYSTEM

BACKGROUND OF THE INVENTION

1. Field of the Invention

The invention relates to an apparatus for the measurement of physiological parameters of blood guided in an extracorporeal circulatory system.

2. Discussion of the Prior Art

The physiological parameters, on the basis of which the efficiency of the extracorporeal circulation can be evaluated, include, inter alia, the blood gas values, particularly the blood's oxygen saturation before and after extracorporeal oxygenation. Only if these values are continually ascertained can the extracorporeal circulation be adapted to blood flow and oxygenation. The hematocrit does, however, also represent an important variable for evaluating the extracorporeal conveyance of blood.

Optical measurement techniques regarding extracorporeally circulating blood, e.g. operations on the cardiovascular system with the assistance of a heart-lung machine (HLM), take advantage of the fact that changes to the microscopic properties of the blood and hence to the physiological parameters which influence them can be deduced from a change in the blood's optical behavior. Both the back-scatter or transmission behavior and the local distribution of absorption rates and radiation distributions are utilized. A particular advantage of optical measurement techniques lies in the fact that the measurement value can usually be ascertained without contact.

An optical measurement arrangement in which a cuvette is inserted into the extracorporeal circulatory system is known for example from U.S. Pat. No. 4,444,498; the cuvette has a planar window through which two LEDs irradiate variable-wavelength light into the blood guided through the cuvette. The light reflected through the window is absorbed by a photosensor and the sensor signal evaluated. On principle, the sensor signal is also dependent on the distance from the cuvette window, on the angle, and on the distance and angle of the light sources.

In general, the hitherto known measurement systems comprise too high an inaccuracy, making it impossible for a control loop, with the inclusion of the HLM, to be realized on the basis of the measurement values achieved. Disposable sensors or, as for example in the above-mentioned arrangement in U.S. Pat. No. 4,444,498, special disposable cuvettes on which the re-usable sensors are mounted are also used in all the known systems.

SUMMARY OF THE INVENTION

Against this background, the invention is based on the object of providing an apparatus which—without the use of disposable sensors and/or disposable cuvettes—is suitable for measuring physiological parameters of blood guided within an extracorporeal circulatory system and makes available the measurement values that permit physiological parameters, particularly blood gas values, and here in particular oxygen saturation, to be controlled.

This object is solved by an apparatus comprising the features of claim 1. Advantageous embodiments are arrived at from the dependent claims.

BRIEF DESCRIPTION OF THE DRAWINGS

The invention will be explained in greater detail as follows on the basis of the drawings in which.

DETAILED DESCRIPTION OF THE INVENTION

Figure 1:
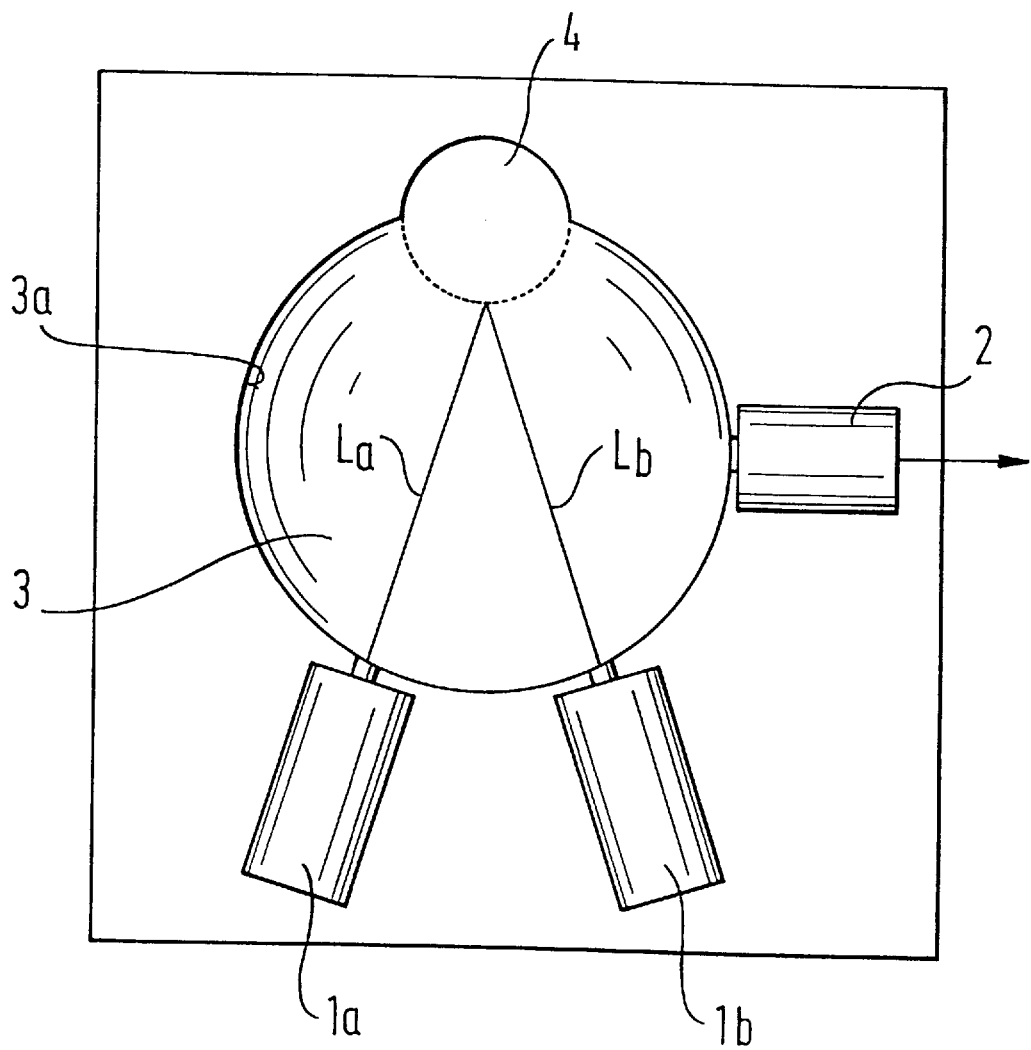
FIG. 1 shows a first exemplary embodiment of the apparatus according to the invention and FIG. 2 shows a second exemplary embodiment of the apparatus according to the invention.

FIG. 1 depicts a first exemplary embodiment of the apparatus according to the invention for measuring physiological parameters of blood conveyed within an extracorporeal circulatory system. The apparatus comprises two light sources 1a and 1b and at least one sensor means 2. The light sources 1a and 1b emit light of a varying wavelength. The light of the one light source 1a has a wavelength of app. 805 nm, since as far as this value is concerned, the spectral diffuse reflection of whole human blood does not depend on the degree of oxygenation (isobestic point). The light of the second light source 1b has a different wavelength, preferably either in the range of 630 nm to 780 nm or in the range of 980 nm to 1080 nm. Within these ranges, the relative diffuse reflection of whole human blood has a comparatively large dependency on the degree of oxygenation, making these ranges particularly well suited for a measurement. The two light sources 1a and 1b emit their light into a spherical cavity 3 which has a diffusely highly reflective inner surface 3a. An evenly mat white surface that follows the law of Lambert's radiator is particularly suitable. Light emitted into the spherical cavity and striking the inner surface is diffusely reflected, thus producing a homogeneous power density on the inner surface of the cavity; this power density can be detected by means of the light sensor means 2 irrespective of the angle. For this purpose, the light sensor means 2 is disposed to receive part of the light propagating within the spherical cavity.

The apparatus according to the invention also has a second cavity 4 into which a tube portion of the extracorporeal blood circulation can be inserted. The second cavity 4 is designed in such a way and is disposed in relation to the first, spherical cavity 3 in such a way that when the tube is inserted, the light $L_a$ and $L_b$ emitted by the light sources 1a and 1b virtually only encounters the boundary surface between the blood and the inner wall of the tube. Apart from negligible scattered light, a direct irradiation onto the inner surface of the first cavity 3 does not take place. Reflection and—if the second cavity 4 completely protrudes into the first, spherical cavity 3—transmission cause part of the irradiated light to return to the first, spherical cavity 3, to encounter the reflective inner surface 3a of the first, spherical cavity 3, and to be optically integrated, as described above, so that the portion of radiation diffusely reflected or transmitted by the blood can be determined by the light sensor means 2 regardless of the angle.

The values ascertained by means of this apparatus according to the invention enable oxygen saturation to be determined extremely accurately, making the apparatus according to the invention suitable for use in terms of control technology within an extracorporeal blood circulation. In this way the output signal of the light sensor means 2 can be used as an input signal of a control loop with which the blood's oxygen content is influenced by controlling an oxygenator through which the blood in the extracorporeal circulatory system is guided.

As indicated in FIG. 1 by means of a dotted line, the second cavity 4 in this exemplary embodiment penetrates the first, spherical cavity 3 regionally. The second cavity 4 can, however, also be disposed to penetrate the first, spherical cavity 3 over its entire cross section. The second cavity 4 may be situated so as to receive the center of the first, spherical cavity 3.

Since a tube portion of the extracorporeal circulation is to be inserted in the second cavity 4, this second cavity 4 advantageously has a cylindrical shape and preferably comprises a circular cross section perpendicular to the longitudinal axis, as shown in FIG. 1. But in a further embodiment, the second cavity 4 may also comprise a cross section that deviates from the circular form, e.g. an elliptical cross section, whereby the principal axis of the elliptical cross section then preferably extends into the first, spherical cavity 3. Since the tube of an extracorporeal circulatory system is usually flexible, its shape can be easily adapted to the shape of the second cavity 4 during insertion. The second cavity 4 is preferably dimensioned such that the tube's outer wall makes contact with the inner wall of the second cavity 4.

Each embodiment in which the second cavity 4 projects into the first, spherical cavity 3, though particularly in the latter cylindrical embodiment with an elliptical cross section, opens up the possibility of using the output signal of the light sensor means to determine the hematocrit of the blood conveyed within the extracorporeal circulation, because the light scattering volume in the blood increases as the hematocrit decreases. In consequence, scattered light increasingly emerges laterally from the cavity 4 and penetrates the cavity 3. The hematocrit can be determined by suitably evaluating that sensor signal portion which is caused by the scattered light.

Figure 2:
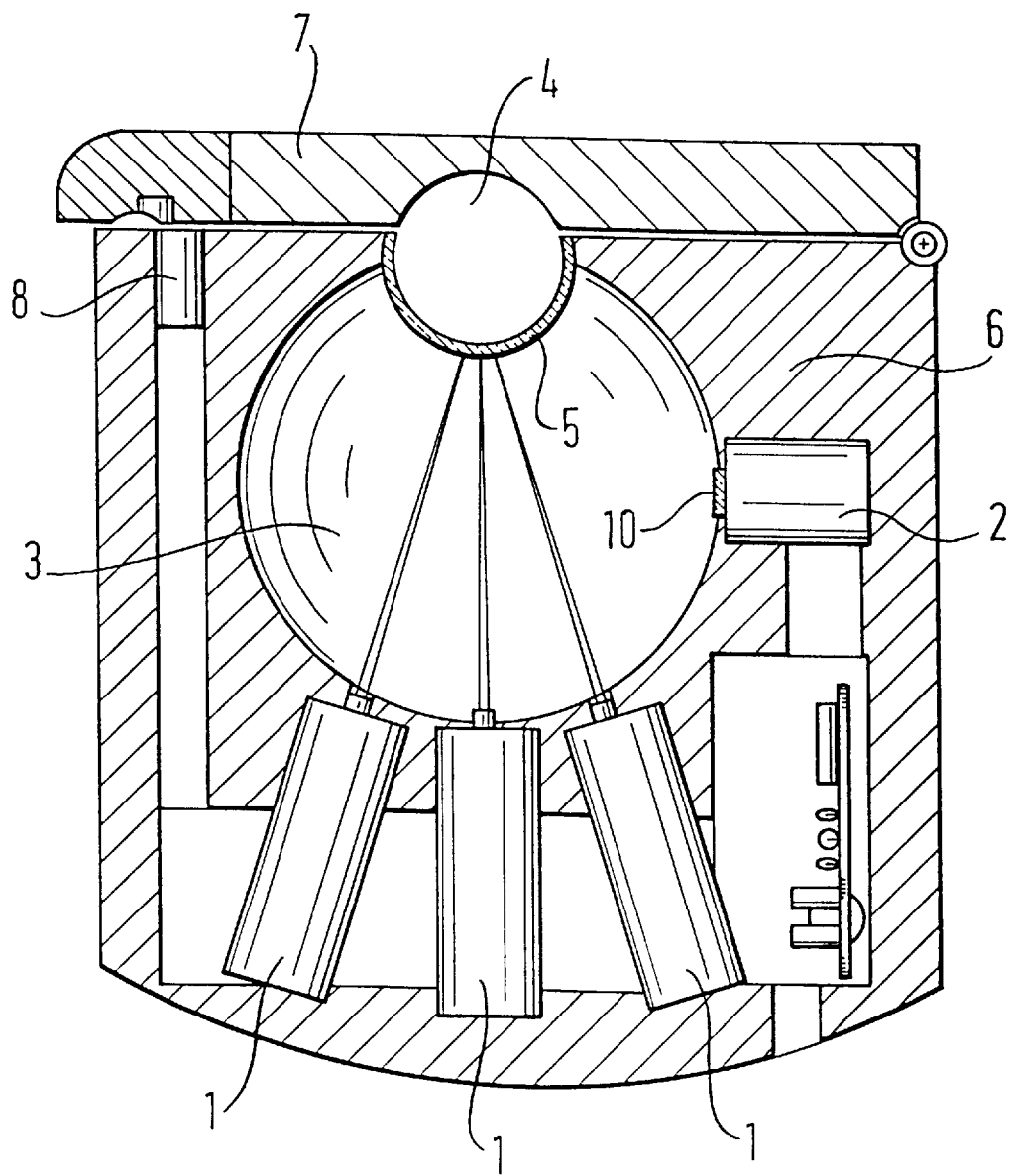

FIG. 2 depicts a second exemplary embodiment which likewise comprises the basic elements of the first exemplary embodiment, but which is provided with other features with the aim of increasing accuracy further and with a view to practical application.

The light sources 1 shown in the second exemplary embodiment are laser light sources and preferably have integrated collimator optics which make it possible to focus accurately the laser light on the boundary surface between the blood and inner tube wall. It is subsequently no longer necessary to adjust the apparatus. The laser light sources 1 of the second exemplary embodiment preferably relate to laser diodes which each advantageously comprise an integrated measuring diode (not depicted) that generates a signal corresponding to the emitted laser light power. This measurement signal can be used to control the laser light power.

In the second exemplary embodiment, a wall element 5 which is permeable to the light emitted by the laser light sources 1 but not to undesirable ambient light is provided between the first, spherical cavity 3 and the second cavity 4. As shown in FIG. 2, the shape of the wall element 5 preferably follows the shape of the second cavity 4 and is consequently always adapted to the shape of the tube portion or helps adapt the flexible tube to the shape of the second cavity 4.

It is likewise identifiable in FIG. 2 that in the second exemplary embodiment, the second cavity 4 is formed only to an extent within a base body 6 which receives at least the first, spherical cavity 3. The laser light sources 1 and the light sensor means 2 are also received in the base body in the exemplary embodiment shown in FIG. 2. The second cavity 4 is completed by a further part which is formed in a cover 7 pivotably mounted on the base body. If the cover 7 is opened, the tube portion can be inserted into that part of the second cavity 4 which is formed within the base body, or it can be taken out at this site. As regards measurements, the cover 7 is closed so that the tube portion is held securely within the second cavity 4 and the irradiation of ambient light is prevented.

To make it impossible for laser light to emerge when the cover is opened and a tube is missing, a detector 8 is preferably provided which detects the closed pivoting position of the cover 7 and the output signal of which is used to interrupt the emission of laser light whenever the cover 7 is opened.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An apparatus adapted to measure physiological parameters of blood conveyed within an extracorporeal circulatory system, comprising:

at least two light sources (1a, 1b) each emitting light of a different wavelength, at least one light sensor means (2), a first, spherical cavity (3) having a reflective inner surface (3a) and into which said light sources (1a, 1b) emit and from which said light sensor means (2) receives part of the light propagating within said first cavity, and a second cavity (4) into which a tube portion of said extracorporeal circulation is inserted such that the light (La, Lb) emitted by said light sources encounters the boundary surface between the blood and an inner wall of said tube and returns to said first cavity (3) at least to an extent by means of reflection and/or transmission.

2. An apparatus according to claim 1, wherein said second cavity (4) penetrates said first cavity (3) at least regionally.

3. An apparatus according to claim 2, wherein said second cavity (4) is cylindrical.

4. An apparatus according to claim 3, wherein said second cavity (4) comprises a circular cross section perpendicular to its longitudinal axis.

5. An apparatus according to claim 3, wherein said second cavity (4) comprises an elliptical cross section perpendicular to its longitudinal axis.

6. An apparatus according to claim 5, wherein said second cavity (4) is disposed such that the principal axis of the elliptical cross section extends into said spherical cavity (3).

7. An apparatus according to claim 1, wherein said light sources are laser light sources (1).

8. An apparatus according to claim 7, wherein one of said laser light sources (1a; 1) emits light at a wavelength of app. 805 nm and the other of said laser light sources (1b; 1) emits light at a wavelength either in the range of 630 to 780 nm or in the range of 980 nm to 1080 nm.

9. An apparatus according to claims 8, wherein said laser light sources (1) are laser diodes.

10. An apparatus according to claim 7, wherein said laser light sources (1) comprise collimator optics.

11. An apparatus according to claims 7, wherein said laser light sources (1) are laser diodes.

12. An apparatus according to claim 11, wherein said laser diodes each comprise an integrated measuring diode which generates a signal corresponding to the emitted laser light power.

13. An apparatus according to claim 1, wherein one of said light sources (1a; 1) emits light at a wavelength of app.

805 nm and the other of said light sources (1*b*; 1) emits light at a wavelength either in the range of 630 to 780 nm or in the range of 980 nm to 1080 nm.

14. An apparatus according to claim.13, wherein said light sources (1) comprise collimator optics.

15. An apparatus according to claim 1, wherein a wall element which is permeable to the light of said light sources but which blocks undesirable ambient light is provided between said first and second cavities.

16. An apparatus according to claim 15, wherein said light sources are laser light sources (1).

17. An apparatus according to claim 16, wherein one of said laser light sources (1*a*; 1) emits light at a wavelength of app. 805 nm and the other of said laser light sources (1*b*; 1) emits light at a wavelength either in the range of 630 to 780 nm or in the range of 980 nm to 1080 nm.

18. An apparatus according to claims 17, wherein said laser light sources (1) are laser diodes.

19. An apparatus according to claim 1, wherein a wall element (10) which is permeable to the light of said light sources but which blocks undesirable ambient light is provided between said first cavity and said light sensor means.

20. An apparatus according to claim 19, wherein said light sources are laser light sources (1).

21. An apparatus according to claim 20, wherein one of said laser light sources (1*a*; 1) emits light at a wavelength of app. 805 nm and the other of said laser light sources (1*b*; 1) emits light at a wavelength either in the range of 630 to 780 nm or in the range of 980 nm to 1080 nm.

22. An apparatus according to claims 21, wherein said laser light sources (1) are laser diodes.

23. An apparatus according to claim 1, wherein said first spherical cavity (3) and a part of said second cavity (4) are formed within a base body (6) and a further part of said second cavity (4) is formed within a body (7) which is movable relative to said base body (6).

24. An apparatus according to claim 23, wherein a wall element which is permeable to the light of said light sources but which blocks undesirable ambient light is provided between said first and second cavities.

25. An apparatus according to claim 24, wherein said light sources are laser light sources (1).

26. An apparatus according to claim 25, wherein one of said laser light sources (1*a*; 1) emits light at a wavelength of app. 805 nm and the other of said laser light sources (1*b*; 1) emits light at a wavelength either in the range of 630 to 780 nm or in the range of 980 nm to 1080 nm.

27. An apparatus according to claims 26, wherein said laser light sources (1) are laser diodes.

28. An apparatus according to claim 23, wherein a wall element (10) which is permeable to the light of said light sources but which blocks undesirable ambient light is provided between said first cavity and said light sensor means.

29. An apparatus according to claim 28, wherein said light sources are laser light sources (1).

30. An apparatus according to claim 29, wherein one of said laser light sources (1*a*; 1) emits light at a wavelength of app. 805 nm and the other of said laser light sources (1*b*; 1) emits light at a wavelength either in the range of 630 to 780 nm or in the range of 980 nm to 1080 nm.

31. An apparatus according to claims 30, wherein said laser light sources (1) are laser diodes.

32. An apparatus according to claim 23, wherein a detector (8) is provided for detecting the closed pivoting position of said body (7) relative to said base body (6).

\* \* \* \* \*